US008034326B2

(12) United States Patent
Hjorth et al.

(10) Patent No.: US 8,034,326 B2
(45) Date of Patent: Oct. 11, 2011

(54) IL-21 VARIANTS

(75) Inventors: Siv Annegrethe Hjorth, Wienervej (DK); Kent Bondensgaard, Vaerlose (DK); Dennis Madsen, Bunkeflostrand (SE)

(73) Assignee: Novo Nordisk A/S, Bagsvaerd (DK)

( * ) Notice: Subject to any disclaimer, the term of this patent is extended or adjusted under 35 U.S.C. 154(b) by 629 days.

(21) Appl. No.: 11/911,815

(22) PCT Filed: Apr. 18, 2006

(86) PCT No.: PCT/EP2006/061635
§ 371 (c)(1),
(2), (4) Date: Jun. 25, 2008

(87) PCT Pub. No.: WO2006/111524
PCT Pub. Date: Oct. 26, 2009

(65) Prior Publication Data
US 2009/0035254 A1 Feb. 5, 2009

Related U.S. Application Data

(60) Provisional application No. 60/676,704, filed on May 2, 2005.

(30) Foreign Application Priority Data

Apr. 18, 2005 (DK) .......................... PA 2005 00562

(51) Int. Cl.
*A61K 38/20* (2006.01)
(52) U.S. Cl. .................. 424/85.2; 530/351; 435/69.52
(58) Field of Classification Search .................. None
See application file for complete search history.

(56) References Cited

U.S. PATENT DOCUMENTS

| | | | |
|---|---|---|---|
| 4,902,502 A | 2/1990 | Nitecki et al. | |
| 5,494,662 A | 2/1996 | Kohji et al. | |
| 5,643,756 A | 7/1997 | Kayman et al. | |
| 6,307,024 B1 | 10/2001 | Novak et al. | |
| 6,423,685 B1 | 7/2002 | Drummond et al. | |
| 6,455,043 B1 | 9/2002 | Grillo-Lopez | |
| 6,929,932 B2 | 8/2005 | Presnell et al. | |
| 7,148,220 B2 | 12/2006 | Vite et al. | |
| 7,186,805 B2 | 3/2007 | Presnell et al. | |
| 7,250,274 B2 | 7/2007 | Chan et al. | |
| 7,276,478 B2 * | 10/2007 | Sivakumar et al. ............. 514/12 |
| 7,528,104 B2 | 5/2009 | Holmes et al. | |
| 2003/0003545 A1 | 1/2003 | Ebner et al. | |
| 2003/0108549 A1 | 6/2003 | Carter et al. | |
| 2003/0186387 A1 | 10/2003 | Ebner et al. | |
| 2004/0009150 A1 | 1/2004 | Nelson et al. | |
| 2004/0228833 A1 | 11/2004 | Costantino et al. | |
| 2006/0024268 A1 | 2/2006 | Kasaian et al. | |

FOREIGN PATENT DOCUMENTS

| | | |
|---|---|---|
| WO | WO 00/53761 | 9/2000 |
| WO | WO 03/028630 A2 | 4/2003 |
| WO | WO 03/040313 | 5/2003 |
| WO | WO 03/082212 A2 | 10/2003 |
| WO | WO 03/087320 | 10/2003 |
| WO | WO 03/103589 | 12/2003 |
| WO | WO 2004/055168 | 7/2004 |
| WO | WO 2004/112703 | 12/2004 |
| WO | WO 2005/035565 | 4/2005 |
| WO | WO 2005/052139 | 6/2005 |
| WO | WO 2006/111524 | 10/2006 |
| WO | WO 2006/135385 | 12/2006 |
| WO | WO 2008/074863 | 6/2008 |

OTHER PUBLICATIONS

Kelso, A., Cytokines: Principles and prospects, Immunology and Cell Biology, vol. 76, pp. 300-317 (1998).
Smyth, M.J. et al., Cytokines in cancer immunity and immunotherapy, Immunological Reviews, vol. 202, pp. 275-293 (2004).
Asao et al., "Cutting Edge: The Common y-Chain is an Indispensable Subunit of the IL-21 Receptor Complex[1]", The Journal of Immunology, Jul. 1, 2001, 167(1), 1-5.
Blohm et al., "Lack of Effector Cell Function and Altered Tetramer Binding of Tumor-Infiltrating Lymphocytes", The Journal of Immunology, Nov. 15, 2002, 169(10), 5522-5530.
Bondensgaard et al., "The Existence of Multiple Conformers of Interleukin-21 Directs Engineering of a Superpotent Analogue", The Journal of Biological Chemistry, Aug. 10, 2007, 282(32), 23326-23336.
Brandhuber et al., "Three-Dimensional Structure of Interleukin-2", Science 238, Dec. 18, 1987, 238(4834) 1707-1709.
Brandt et al., "The B7 Family Member B7-H6 is a tumor cell ligand for the activating natural killer cell receptor NKp30 in Humans," Journal Exp. Med., Jun. 15, 2009, 206(7), 1495-1503.
Brandt, C et al., Journal of Leukocyte Biology Suppl. S 119, Nov. 8-11, 2001, 2 pages.
Collins, et al., "IL-21 and IL-21 Receptor A New Cytokine pathway modulates innate and adaptive immunity", Immunological Research, 2003, 28(2), 131-140.
Communication from the EP Examining Division dated Jun. 3, 2009, Issued in corresponding EP Application No. 04762905.0, 8 pages.
Delgado et al., "Critical Reviews in Therapeutic Drug Carrier Systems", 1992, 9(3-4), 249-304.
Dunn et al., "Cancer Immunoediting: From Immunosurveillance to Tumor Escape", Nature Immunology, Nov. 2002, 3(11), 991-998.
Genmab "Genmab Presents new Humax-CD20 and Humax-EFGr Pre-Clinical Data", Genmab New Release, Feb. 7, 2003, 1-3.
Hage et al., "Crystal Structure of the Interleukin-4/Receptor a Chain Complex Reveals a Mosaic Binding Interface", Cell Press, Apr. 16, 1999, 97(2), 271-281.
International Preliminary Report on Patentability issued Jun. 24, 2009 in corresponding International Application No. PCT/EP2007/064326, 6 pages.

(Continued)

Primary Examiner — Dong Jiang
(74) Attorney, Agent, or Firm — Woodcock Washburn LLP

(57) ABSTRACT

IL-21 variant are provided wherein amino acids have been deleted and/or substituted in the region consisting of amino acid No. 65-96.

17 Claims, 2 Drawing Sheets

OTHER PUBLICATIONS

Figure 1:
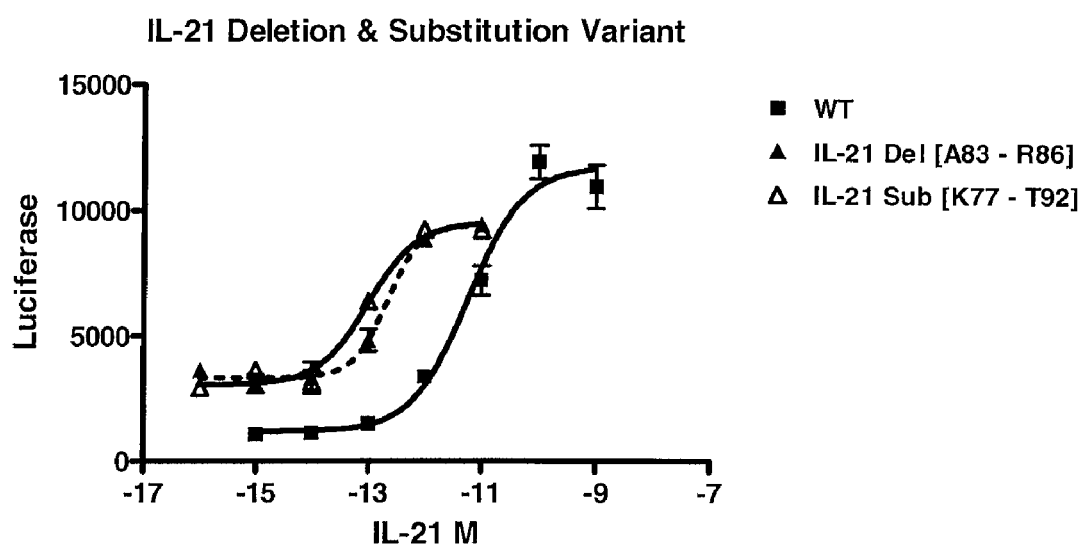

Kataki et al., "Tumor infiltrating lymphocytes and macrophages have a potential dual role in lung cancer by supporting both host-defense and tumor progression", Nov. 2002, 140(5), 320-328.

Katre, "The Conjugation of proteins with polyethylene glycol and other polymers: Altering properties of proteins to enhance their therapeutic potential", Advanced Drug Delivery Reviews, Jan.-Apr. 1993, 10(1), 91-114.

Khong et al., "Natural Selection of Tumor variants in the generation of "tumor escape" phenotypes", Nat. Immunol., Nov. 2002, 3(11), 999-1005.

Kinstler et al., "Mono-N-Terminal poly(ethylene glycol)—protein conjugates", Advanced Drug Delivery Reviews, Jun. 7, 2002, 54(4), 477-485.

Knauf et al., "Relationships of effective molecular size to systemic clearance in rats of recombinant interleukin-2 chemically modified with water-soluble polymers", J. Biol. Chem. Oct. 15, 1988, 263(29), 15064-15070.

Leonard et al., "Interleukin-21: A Modulator of Lymphoid Proliferation, Apoptosis and Differentiation", Nature Reviews Immunology, Sep. 2005, 5(9), 688-698.

Mehta et al., "Biology of IL-21 and the IL-21 Receptor", Immunological Reviews, Munksgaard XX, Dec. 2004, 202(1), 84-95.

Mott et al., "The Solution Structure of the F42A Mutant of Human Interleukin 2", Journal of Molecular Biology, Apr. 14, 1995, 247(5), 979-994.

Olosz et al., "Structural Basis for Binding Multiple Ligands by the Common Cytokine Receptor Y-Chain", The Journal of Biological Chemistry, Jan. 28, 2002, 277(14), 12047-12052.

Parish-Novak et al., "Interleukin 21 and its receptor are involved in NK Cell expansion and Regulation of lymphocyte function", Nov. 2, 2000, 408(6808), 57-63.

PCT Application No: PCT/EP2007/064326, Preliminary Report on Patentability, Filing date: Dec. 20, 2007, Mailing Date: Jun. 6, 2009, 6 pages.

Powers et al., "Three-Dimensional Solution Structure of Human Interleukin-4 by Multidimensional Heteronuclear Magnetic Resonance Spectroscopy", Science, Jun. 19, 1992, 256(5064), 1673-1677.

Response to the Jun. 3, 2009 Communication from the EP Examining Division, EP 04762905.0, dated Jan. 6, 2010, 6 pages.

Sivakumar et al., "Interleukin-21 is a T-Helper cytokine that regulates humoral immunity and cell mediated anti-tumor response", Immunology Black Well Publishing OxFord GB, Mar. 26, 2004, 112, 117-182.

Stengaard-Pedersen et al. "Inherited Deficiency of Mannan-Binding Lectin-Associated Serine Protease 2", New England Journal of Medicine, Aug. 7, 2003, 349(6), 554-560.

Tony et al., "Design of Human Interleukin-4 Antagonists inhibiting Interleukin-4-dependent and Interleukin-13-dependent responses in T-cells and B-cells with high efficiency", European Journal of Biochemistry, Jun. 23, 1994, 225(2), 659-665.

Wang et al., "Structure of the Quaternary Complex of Interleukin-2 with it's A,B, and Yc Receptors", Science, Nov. 18, 2005, 310(5751), 1159-1163.

Wlodaver, A. et al., "Crystal Structure of Human Recombinant Interleukin-4 at 2.25 A Resolution", Febs Letters, Aug. 31, 1992, 309(1), 59-64.

Zalipsky "Chemistry of Polyethylene Glycol Conjugates with biologically active molecules", Advanced Drug Delivery Reviews, Sep. 1995, 16(2-3), 157-182.

Zhang et al., "Functional Epitope of Common Y Chain for Interleukin-4 Binding", European Journal of Biochemistry, Jan. 2002, 269(5), 1490-1499.

Zhang et al., "Human IL-21 and IL-4 bind to partially overlapping epitopes of Common Y-Chain", Biochemical and Biophysical Research Communications, Jan. 10, 2003, 300(2), 291-296.

Zhang et al., "Intratumoral T Cells, Recurrence, and Survival in Epithelial Ovarian Cancer", New England Journal of Medicine, Jan. 16, 2003, 348(3), 203-213.

Doerks et al., "Protein annotation: detective work for function prediction", Trends in Genetics, Jun. 1998, 14(6), 248-250.

Ngo et al., "Computational complexity, protein structure prediction, and the Levinthal paradox", The Protein Folding Problems and Tertiary Structure Prediction, 1994, 492-495.

Skolnick et al., "From genes to protein structure and function: novel applications of computational approaches in the genomic era", Trends in Biotech, Jan. 2000, 18(1), 34-39.

Wells, "Additivity of Mutational Effects in Proteins", Biochemistry, Sep. 18, 1990, 29, 8509-8517.

* cited by examiner

IL-21 VARIANTS

CROSS-REFERENCE TO RELATED APPLICATIONS

This application is the U.S. National Stage (filed under 35 U.S.C. §371) of International Patent Application PCT/EP2006/061635 (published as WO 2006/111524), filed Apr. 18, 2006, and claims the benefit of Danish Patent Application PA 2005 00562, filed Apr. 18, 2005, and U.S. Provisional Patent Application 60/676,704, filed May 2, 2005.

FIELD OF THE INVENTION

The present invention is concerned with new variants of IL-21, said variants being useful for therapy.

BACKGROUND OF THE INVENTION

IL-21 peptides were first disclosed in WO 00/53761 as SEQ ID No: 2. The pro-peptide is a 161 amino acid residue peptide. For convenience, the sequence is repeated in the present application as SEQ ID No: 1. It was initially believed that the mature peptide was the peptide consisting of amino acids No. 33 to 162 of SEQ ID No: 1; however more recently (WO 2004/112703) it has been suggested that the mature peptide is, in fact, amino acids No. 30 to 162, which is disclosed as SEQ ID No: 11 with an additional N-terminal methionine in the present application.

IL-21 is a cytokine. Cytokines generally stimulate proliferation, differentiation and/or activation of cells of the hematopoietic lineage or participate in the immune and inflammatory response mechanisms of the body. The interleukins are a family of cytokines that mediate immunological responses by producing various cytokines, and they effect adaptive immunity to antigens. Mature T cells can be activated, i.e., by an antigen or other stimulus, to produce, for example, cytokines, biochemical signaling molecules, or receptors that further influence the fate of the T cell population.

Cytokines produced by the T cell have been classified as type 1 and type 2 (Kelso, A. *Immun. Cell Biol.* 76:300-317, 1998). Type 1 cytokines include IL-2, IFN-γ, LT-α, and they are involved in inflammatory responses, viral immunity, intracellular parasite immunity and allograft rejection. Type 2 cytokines include IL-4, IL-5, IL-6, IL-10 and IL-13, and they are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Mature T cells can be activated, i.e., by an antigen or other stimulus, to produce, for example, cytokines, biochemical signaling molecules, or receptors that further influence the fate of the T cell population.

B cells can be activated via receptors on their cell surface including B cell receptor and other accessory molecules to perform accessory cell functions, such as production of cytokines and antibodies.

Natural killer (NK) cells have a common progenitor cell with T cells and B cells, and play a role in immune surveillance. NK cells, which comprise up to 15% of blood lymphocytes, do not express antigen receptors, and therefore do not use MHC recognition as requirement for binding to a target cell. NK cells are involved in the recognition and killing of certain tumor cells and virally infected cells. In vivo, NK cells are believed to require activation, however, in vitro, NK cells have been shown to kill some types of tumor cells via KIR ligand dependent activation.

In spite of the efficacy shown by IL-21 in the treatment of various diseases, there remains a need for variants of IL-21 with improved or alternative properties, such as activity, selectivity, stability, and circulation time or biological half-life, to fulfil medical needs.

SUMMARY OF THE INVENTION

The present inventors have surprisingly found that the activity of IL-21 is largely maintained or even improved when amino acids in the region 66 to 98 are deleted and/or substituted. In the present context, the amino acid numbering is with respect to the mature 133 amino acid peptide (amino acid No. 30 to 162 of the pro-peptide, SEQ ID No: 1). This sequence is given as SEQ ID No: 11 including an additional N-terminal methionine giving a 134 amino acid peptide. SEQ ID No: 2 is amino acid No. 30 to 162 of the pro-peptide, SEQ ID No: 1 without an additional N-terminal methionine giving a 133 amino acid peptide. Accordingly, in one embodiment, the invention relates to a peptide comprising a) a first sequence obtained by deleting and/or substituting one or more amino acid in the region consisting of amino acid No. 65 to amino acid No. 96 of SEQ ID No: 2; or b) a sequence obtained by conservatively substituting up to 10 amino acids in said first sequence.

In one embodiment, the invention provides the use of a peptide of the present invention in therapy.

In one embodiment, the invention relates to a pharmaceutical composition comprising a peptide of the present invention.

In one embodiment, the invention provides a therapeutic method, the method comprising the administration of a therapeutically effective amount of a peptide of the present invention to a patient in need thereof.

In one embodiment, the invention relates to the use of peptide of the present invention in the manufacture of a medicament.

In one embodiment, the invention relates to nucleic acid construct encoding a peptide of the present invention; to vectors comprising said constructs; and to host cells comprising said vectors.

In one embodiment, the invention relates to specific antibodies against a peptide of the present invention.

FIGURES

FIG. 1 Baf3/hIL-21R/Stat-Luc analysis of IL-21 variants

Supernatant from HEK293-FS cells transfected with the indicated IL-21 constructs were analyzed in the BAf3-hIL-21R/Stat-Luc reporter assay. Protein content was estimated by ELISA.

■ Wild type IL-21; ▲—IL-21 deletion mutant [A83-R86] (SEQ ID No: 3); and Δ IL-21 variant in which the sequence [K77-T92] has been substituted (SEQ ID No: 7).

Figure 2:
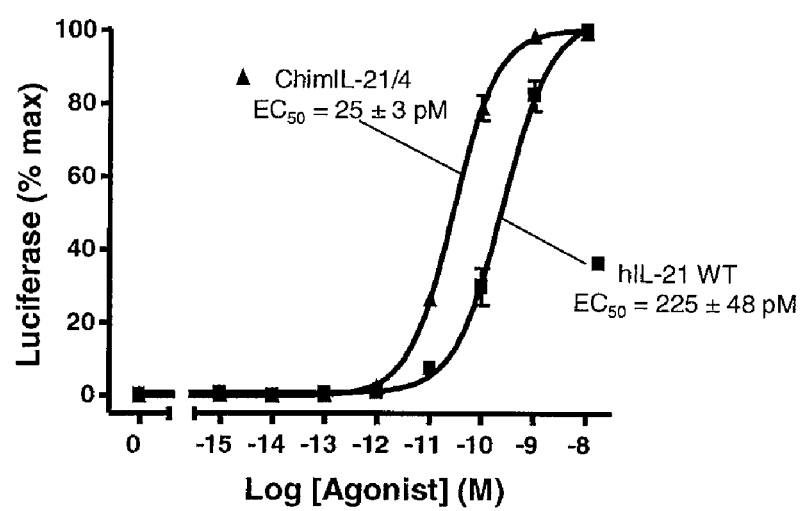

FIG. 2 Dose-response curves for hIL-WT and ChimIL-21/4.

Purified proteins were analyzed in a reporter assay using the Baf3/hIL-21Ra cells. The curves represent a sum of independent experiments (n=4) all performed in triplicate. Activity is expressed as percentage of maximal response. EC50 values±S.E.M. obtained are presented. Chim-IL21 is the IL-21 sub[K77-T92].

DEFINITIONS

In the present context "a" is intended to indicate one or more.

In the present context, the term "peptide" is intended to indicate two or more amino acids which are bonded by a peptide bond. Said amino acids may be codable or non-codable, and the term also includes peptide derivatives, wherein one or more amino acid in the peptide has been chemically substituted, e.g. by PEG or a lipophilic group. The terms "peptide" and "polypeptide" are used interchangeably and are intended to indicate the same.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

A "therapeutically effective amount" of a peptide as used herein means an amount sufficient to cure, alleviate or partially arrest the clinical manifestations of a given disease and its complications. An amount adequate to accomplish this is defined as "therapeutically effective amount". Effective amounts for each purpose will depend on the type and severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active peptides to prevent the onset of the symptoms or complications. The patient to be treated is preferably a mammal, in particular a human being, but it may also include animals, such as dogs, cats, cows, sheep and pigs. It is to be understood, that therapeutic and prophylactic (preventive) regimes represent separate aspects of the present invention.

DESCRIPTION OF THE INVENTION

In one embodiment, the invention relates to a peptide comprising
a) a first sequence obtained by deleting and/or substituting one or more amino acid in the region consisting of amino acid No. 65 to amino acid No. 96 of SEQ ID No: 2;
or
b) a sequence obtained by conservatively substituting up to 10 amino acids in said first sequence. In particular at least 2, such as at least 3, such as at least 4, such as at least 5, such as at least 6 amino acids have been deleted and/or substituted in said first sequence.

The invention also relates to peptides obtained by conservative substitutions in the more specific embodiments of the peptide of the present invention described below.

In particular, up to 10, such as 1, 2, 3, 4, 5, 6, 7, 8, 9 or 10 amino acids may be conservatively substituted. In the present context a substitution is conservative when one amino acid residue is substituted by another amino acid residue from the same group, i.e. by another amino acid residue with similar properties. Amino acid may conveniently be divided in the following groups based on their properties: Basic amino acids (such as arginine and lysine), acidic amino acids (such as glutamic acid and aspartic acid), polar amino acids (such as glutamine, histidine, methionine and asparagine), aliphatic or hydrophobic amino acids (such as alanine, leucine, isoleucine, valine), aromatic amino acids (such as phenylalanine, tryptophan, tyrosine) and small amino acids (such as glycine, alanine, serine, and threonine).

In one embodiment, the invention relates to a peptide comprising the sequence obtained by deleting and/or substituting one or more amino acid in the region consisting of amino acid No. 83 to amino acid No. 86 of SEQ ID No: 2.

In one embodiment, the invention relates to a peptide comprising the sequence obtained by deleting and/or substituting one or more amino acid in the region consisting of amino acid No. 83 to amino acid No. 88 of SEQ ID No: 2.

In one embodiment, the invention relates to a peptide comprising the sequence obtained by deleting and/or substituting one or more amino acid in the region consisting of amino acid No. 83 to amino acid No. 90 of SEQ ID No: 2.

In one embodiment, the invention relates to a peptide comprising the sequence obtained by deleting and/or substituting one or more amino acid in the region consisting of amino acid No. 82 to amino acid No. 88 of SEQ ID No: 2.

In one embodiment, the invention relates to a peptide comprising the sequence obtained by deleting and/or substituting one or more amino acid in the region consisting of amino acid No. 77 to amino acid No. 92 of SEQ ID No: 2.

In one embodiment, the invention relates to a peptide comprising the sequence obtained by deleting and/or substituting one or more amino acid in the region consisting of amino acid No. 71 to amino acid No. 92 of SEQ ID No: 2.

In one embodiment, the invention relates to a peptide comprising the sequence obtained by deleting and/or substituting one or more amino acid in the region consisting of amino acid No. 65 to amino acid No. 92 of SEQ ID No: 2.

In one embodiment, the invention relates to a peptide comprising the sequence obtained by deleting and/or substituting one or more amino acid in the region consisting of amino acid No. 77 to amino acid No. 96 of SEQ ID No: 2.

In one embodiment, the invention relates to a peptide comprising the sequence obtained by deleting one or more amino acid in the region consisting of amino acid No. 83 to amino acid No. 86 of SEQ ID No: 2.

In one embodiment, the invention relates to a peptide comprising the sequence obtained by deleting one or more amino acid in the region consisting of amino acid No. 83 to amino acid No. 88 of SEQ ID No: 2.

In one embodiment, the invention relates to a peptide comprising the sequence obtained by deleting one or more amino acid in the region consisting of amino acid No. 83 to amino acid No. 90 of SEQ ID No: 2.

In one embodiment, the invention relates to a peptide comprising the sequence obtained by deleting one or more amino acid in the region consisting of amino acid No. 82 to amino acid No. 88 of SEQ ID No: 2.

In one embodiment, the invention relates to a peptide comprising the sequence obtained by substituting and deleting two or more amino acid in the region consisting of amino acid No. 77 to amino acid No. 92 of SEQ ID No: 2.

In one embodiment, the invention relates to a peptide comprising the sequence obtained by substituting and deleting two or more amino acid in the region consisting of amino acid No. 71 to amino acid No. 92 of SEQ ID No: 2.

In one embodiment, the invention relates to a peptide comprising the sequence obtained by substituting and deleting two or more amino acid in the region consisting of amino acid No. 65 to amino acid No. 92 of SEQ ID No: 2.

In one embodiment, the invention relates to a peptide comprising the sequence obtained by substituting and deleting two or more amino acid in the region consisting of amino acid No. 77 to amino acid No. 96 of SEQ ID No: 2.

In one embodiment, the invention relates to a peptide obtained by deleting and/or substituting one or more amino acid in the region consisting of amino acid No. 83 to amino acid No. 86 of SEQ ID No: 2.

In one embodiment, the invention relates to a peptide obtained by deleting and/or substituting one or more amino acid in the region consisting of amino acid No. 83 to amino acid No. 88 ID NO: 2.

In one embodiment, the invention relates to a peptide obtained by deleting and/or substituting one or more amino acid in the region consisting of amino acid No. 83 to amino acid No. 90 of SEQ ID No: 2.

In one embodiment, the invention relates to a peptide obtained by deleting and/or substituting one or more amino acid in the region consisting of amino acid No. 82 to amino acid No. 88 of SEQ ID No: 2.

In one embodiment, the invention relates to a peptide obtained by deleting and/or substituting one or more amino acid in the region consisting of amino acid No. 77 to amino acid No. 92 of SEQ ID No: 2.

In one embodiment, the invention relates to a peptide obtained by deleting and/or substituting one or more amino acid in the region consisting of amino acid No. 71 to amino acid No. 92 of SEQ ID No: 2.

In one embodiment, the invention relates to a peptide obtained by deleting and/or substituting one or more amino acid in the region consisting of amino acid No. 65 to amino acid No. 92 of SEQ ID No: 2.

In one embodiment, the invention relates to a peptide obtained by deleting and/or substituting one or more amino acid in the region consisting of amino acid No. 77 to amino acid No. 96 of SEQ ID No: 2.

In one embodiment, the invention relates to a peptide obtained by deleting one or more amino acid in the region consisting of amino acid No. 83 to amino acid No. 86 of SEQ ID No: 2.

In one embodiment, the invention relates to a peptide obtained by deleting one or more amino acid in the region consisting of amino acid No. 83 to amino acid No. 88 SEQ ID No: 2.

In one embodiment, the invention relates to a peptide obtained by deleting one or more amino acid in the region consisting of amino acid No. 83 to amino acid No. 90 of SEQ ID No: 2.

In one embodiment, the invention relates to a peptide obtained by deleting one or more amino acid in the region consisting of amino acid No. 82 to amino acid No. 88 of SEQ ID No: 2.

In one embodiment, the invention relates to a peptide obtained by substituting and deleting two or more amino acid in the region consisting of amino acid No. 77 to amino acid No. 92 of SEQ ID No: 2.

In one embodiment, the invention relates to a peptide obtained by substituting and deleting two or more amino acid in the region consisting of amino acid No. 71 to amino acid No. 92 of SEQ ID No: 2.

In one embodiment, the invention relates to a peptide obtained by substituting and deleting two or more amino acid in the region consisting of amino acid No. 65 to amino acid No. 92 of SEQ ID No: 2.

In one embodiment, the invention relates to a peptide obtained by substituting and deleting two or more amino acid in the region consisting of amino acid No. 77 to amino acid No. 96 of SEQ ID No: 2.

As discussed above, IL-21 is expressed as a 161 amino acid peptide, but is post-translationally processed by removing amino acid No. 1 to 29 or by removing amino acid No. 1 to 31. The present invention is thus intended also to include peptides comprising the sequence obtained by removing and/or deleting one or more amino acid from the region consisting of amino acid No. 65 to amino acid No. 96, wherein the N-terminal has been extended by the N-terminal 29 amino acids from SEQ ID No: 1 or with the N-terminal 31 amino acids from SEQ ID No: 1.

When peptides are expressed in mammalian cells, such as CHO cells, an N-terminal signal peptide is often removed by a so-called signal peptidase leading to the mature peptide. It is well-known in the art that to express the same heterologous peptides in prokaryotic cells, such as e.g. *E. coli*, it is often necessary—via recombinant technology well-known to those skilled in the art—to introduce an additional N-terminal methionine to the sequence of the mature peptide. The present invention is thus intended to include the above mentioned peptides with or without an N-terminal methionine.

In one embodiment, the invention relates to peptides selected from

A) SEQ ID No: 3 (deletion A83-R86), SEQ ID No: 4 (deletion A83-K88), SEQ ID No: 5 (deletion A83-R90), and SEQ ID No: 6 (deletion N82-K88); and B) the peptides of A) with an additional N-terminal Met C) the peptides of A)-B), wherein up to 10 amino acids have been conservatively substituted.

In one embodiment, the invention relates to peptides selected from

D) SEQ ID No: 7 (K77-T92 substitution), SEQ ID No: 8 (I71-T92 substitution), SEQ ID No: 9 (R65-T92 substitution), and SEQ ID No: 10 (K77-C96) substitution; and E) the peptides of D) with an additional N-terminal Met; and F) the peptides of D-E) wherein up to 10 amino acids have been conservatively substituted.

In one embodiment, the invention is related to pharmaceutically acceptable salts of the above peptides.

The peptides of the present invention may be further derivatized by the attachment of groups which will effect an extension of the circulation time in plasma and/or biological half-life, or which will reduce any immunogenicity. It is well-known in the art that such effects may be obtained by the attachment of certain groups, such as polyethylene glycol (PEG); lipophilic groups, such as fatty acids; plasma proteins, such as albumin; or albumin binding moieties. For examples from the art, see e.g. WO 01/79271, U.S. Pat. No. 5,739,208, and WO 03/44056.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a protein of interest. The construct may optionally contain other nucleic acid segments.

The nucleic acid construct of the invention encoding the protein of the invention may suitably be of genomic or cDNA origin, for instance obtained by preparing a genomic or cDNA library and screening for DNA sequences coding for all or part of the protein by hybridization using synthetic oligonucleotide probes in accordance with standard techniques (cf. Sambrook et al., supra). For the present purpose, the DNA sequence encoding the protein is preferably of human origin, i.e. derived from a human genomic DNA or cDNA library. In particular, the DNA sequence may be of human origin, e.g. cDNA from a particular human organ or cell type or a gene derived from human genomic DNA.

The nucleic acid construct of the invention encoding the peptide may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or Saiki et al., *Science* 239 (1988), 487-491.

The nucleic acid construct is preferably a DNA construct which term will be used exclusively in the following.

Recombinant Vector

In a further aspect, the present invention relates to a recombinant vector comprising a DNA construct of the invention. The recombinant vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the protein of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the protein.

The promoter may be any DNA sequence which shows transcriptional activity in the host cell of choice and may be derived from genes encoding proteins either homologous or heterologous to the host cell.

Examples of suitable promoters for directing the transcription of the DNA encoding the protein of the invention in mammalian cells are the SV40 promoter (Subramani et al., *Mol. Cell. Biol.* 1 (1981), 854-864), the MT-1 (metallothionein gene) promoter (Palmiter et al., *Science* 222 (1983), 809-814) or the adenovirus 2 major late promoter.

An example of a suitable promoter for use in insect cells is the polyhedrin promoter (U.S. Pat. No. 4,745,051; Vasuvedan et al., *FEBS Lett.* 311, (1992) 7-11), the P10 promoter (J. M. Vlak et al., *J. Gen. Virology* 69, 1988, pp. 765-776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., *J. Biol. Chem.* 255 (1980), 12073-12080; Alber and Kawasaki, *J. Mol. Appl. Gen.* 1 (1982), 419-434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652-654) promoters.

Examples of suitable promoters for use in filamentous fungus host cells are, for instance, the ADH3 promoter (McKnight et al., *The EMBO J.* 4 (1985), 2093-2099) or the tpiA promoter. Examples of other useful promoters are those derived from the gene encoding *A. otyzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. otyzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylosidase gene, or by the phage Lambda $P_R$ or $P_L$ promoters or the *E. coli* lac, trp or tac promoters.

The DNA sequence encoding the protein of the invention may also, if necessary, be operably connected to a suitable terminator, such as the human growth hormone terminator (Palmiter et al., *op. cit.*) or (for fungal hosts) the TPI1 (Alber and Kawasaki, *op. cit.*) or ADH3 (McKnight et al., *op. cit.*) terminators. The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant vector of the invention may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2μ replication genes REP 1-3 and origin of replication.

When the host cell is a bacterial cell, sequences enabling the vector to replicate are DNA polymerase III complex encoding genes and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125-130), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

To direct a protein of the present invention into the secretory pathway of the host cells, a secretory signal sequence (also known as a leader sequence, prepro sequence or pre sequence) may be provided in the recombinant vector. The secretory signal sequence is joined to the DNA sequence encoding the protein in the correct reading frame. Secretory signal sequences are commonly positioned 5' to the DNA sequence encoding the protein. The secretory signal sequence may be that normally associated with the protein or may be from a gene encoding another secreted protein.

For secretion from yeast cells, the secretory signal sequence may encode any signal peptide which ensures efficient direction of the expressed protein into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., *Nature* 289, 1981, pp. 643-646), a modified carboxypeptidase signal peptide (cf. L. A. Valls et al., *Cell* 48, 1987, pp. 887-897), the yeast BAR1 signal peptide (cf. WO 87/02670), or the yeast aspartic protease 3 (YAP3) signal peptide (cf. M. Egel-Mitani et al., *Yeast* 6, 1990, pp. 127-137).

For efficient secretion in yeast, a sequence encoding a leader peptide may also be inserted downstream of the signal sequence and upstream of the DNA sequence encoding the protein. The function of the leader peptide is to allow the expressed protein to be directed from the endoplasmic reticulum to the Golgi apparatus and further to a secretory vesicle for secretion into the culture medium (i.e. exportation of the protein across the cell wall or at least through the cellular membrane into the periplasmic space of the yeast cell). The leader peptide may be the yeast α-factor leader (the use of which is described in e.g. U.S. Pat. No. 4,546,082, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the present protein, the promoter and optionally the terminator and/or secretory signal sequence, respectively, and to insert them into suitable vectors containing the information necessary for replication, are well known to persons skilled in the art (cf., for instance, Sambrook et al., *op. cit.*).

Host Cells

The host cell into which the DNA construct or the recombinant vector of the invention is introduced may be any cell which is capable of producing the present protein and includes bacteria, yeast, fungi and higher eukaryotic cells.

Examples of bacterial host cells which, on cultivation, are capable of producing the protein of the invention are gram-positive bacteria such as strains of *Bacillus*, such as strains of *B. subtilis*, *B. licheniformis*, *B. lentus*, *B. brevis*, *B. stearothermophilus*, *B. alkalophilus*, *B. amyloliquefaciens*, *B. coagulans*, *B. circulans*, *B. lautus*, *B. megatherium* or *B. thuringiensis*, or strains of *Streptomyces*, such as *S. lividans* or *S. murinus*, or gramnegative bacteria such as *Escherichia coli*. The transformation of the bacteria may be effected by protoplast transformation or by using competent cells in a manner known per se (cf. Sambrook et al., supra).

When expressing the protein in bacteria such as *E. coli*, the protein may be retained in the cytoplasm, typically as insoluble granules (known as inclusion bodies), or may be directed to the periplasmic space by a bacterial secretion sequence. In the former case, the cells are lysed and the granules are recovered and denatured after which the protein is refolded by diluting the denaturing agent. In the latter case, the protein may be recovered from the periplasmic space by disrupting the cells, e.g. by sonication or osmotic shock, to release the contents of the periplasmic space and recovering the protein.

Examples of suitable mammalian cell lines are the COS (ATCC CRL 1650), BHK (ATCC CRL 1632, ATCC CCL 10), CHL (ATCC CCL39) or CHO (ATCC CCL 61) cell lines. Methods of transfecting mammalian cells and expressing DNA sequences introduced in the cells are described in e.g. Kaufman and Sharp, *J. Mol. Biol.* 159 (1982), 601-621; Southern and Berg, *J. Mol. Appl. Genet.* 1 (1982), 327-341; Loyter et al., *Proc. Natl. Acad. Sci. USA* 79 (1982), 422-426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841-845.

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous proteins therefrom are described, e.g. in U.S. Pat. No. 4,599,311, U.S. Pat. No. 4,931,373, U.S. Pat. Nos. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the protein of the invention may be preceded by a signal sequence and optionally a leader sequence, e.g. as described above. Further examples of suitable yeast cells are strains of *Kluyveromyces*, such as *K. lactis, Hansenula*, e.g. *H. polymorpha*, or *Pichia*, e.g. *P. pastoris* (cf. Gleeson et al., *J. Gen. Microbiol.* 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of proteins is described in, e.g., EP 272 277 and EP 230 023. The transformation of *F. oxysporum* may, for instance, be carried out as described by Malardier et al., 1989, Gene 78: 147-156.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous proteins therein may be performed as described in U.S. Pat. No. 4,745,051; U.S. Pat. No. 4,879,236; U.S. Pat. Nos. 5,155,037; 5,162,222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting the expression of the present protein, after which the resulting protein is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The protein produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of protein in question.

Peptides of the present invention can be used to raise antibodies that specifically bind to the peptides of the present invention. In the present context, "antibodies" include monoclonal and polyclonal antibodies, and antigen-binding fragments thereof, such as $F(ab')_2$ and Fab fragments, including genetically engineered antibodies and humanized antibodies. Antibodies are said to be specific if they bind to a peptide of the present invention with a $K_a$ greater than or equal to $10^7$ $M^{-1}$. Methods for preparing antibodies are disclosed in e.g. Hurrell J. G. R. (Ed.) *Monoclonal Hybridoma Antibodies: Techniques and Applications*, CRC Press, Boca Raton, Fla., 1982 and Sambrok, *Molecular Cloning: A Laboratory Manual*, Cold Spring Harbour, New York, 1989.

IL-21 has been implicated in the treatment of viral diseases, such as hepatitis B Virus, Hepatitis C virus, Human Immunodeficiency Virus, Respiratory Syncytial Virus, Eppstein-Barr Virus, Influenza Virus, Cytomegalovirus, Herpes-Virus and Severe Acute Respiratory Syndrome.; allergic diseases, such as asthma, allergic rhinitis or allergic diseases in the skin; parasitic diseases, such as helminthic infection, autoimmune diseases, such as allograft rejection and diabetes; and cancer.

In the present context, "cancer" refers to any neoplastic disorder, including such cellular disorders such as sarcoma, carcinoma, melanoma, leukemia, lymphoma, cancers in the breast, head and neck, ovaries, bladder, lung, pharynx, larynx, oesophagus, stomach, small intestines, liver, pancreas, colon, female reproductive tract, male reproductive tract, prostate, kidneys and central nervous system. In particular, "cancer" is intended to indicate non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin.

In more specific aspects of the invention the terms "neoplastic disorders", "cancer" or "tumor growth" are to be understood as referring to all forms of neoplastic cell growth, including both cystic and solid tumors, bone and soft tissue tumors, including both benign and malignant tumors, including tumors in anal tissue, bile duct, bladder, blood cells, bone, bone (secondary), bowel (colon & rectum), brain, brain (secondary), breast, breast (secondary), carcinoid, cervix, children's cancers, eye, gullet (oesophagus), head & neck, kaposi's sarcoma, kidney, larynx, leukaemia (acute lymphoblastic), leukaemia (acute myeloid), leukaemia (chronic lymphocytic), leukaemia (chronic myeloid), leukaemia (other), liver, liver (secondary), lung, lung (secondary), lymph nodes (secondary), lymphoma (hodgkin's), lymphoma (non-hodgkin's), melanoma, mesothelioma, myeloma, ovary, pancreas, penis, prostate, skin, soft tissue sarcomas, stomach, testes, thyroid, unknown primary tumour, vagina, vulva, womb (uterus).

Soft tissue tumors include Benign schwannoma Monosomy, Desmoid tumor, Lipo-blastoma, Lipoma, Uterine leiomyoma, Clear cell sarcoma, Dermatofibrosarcoma, Ewing sarcoma, Extraskeletal myxoid chondrosarcoma, Liposarcoma myxoid, Liposarcoma, well differentiated, Alveolar rhabdomyosarcoma, and Synovial sarcoma.

Specific bone tumor include Nonossifying Fibroma, Unicameral bone cyst, Enchon-droma, Aneurysmal bone cyst, Osteoblastoma, Chondroblastoma, Chondromyxofibroma, Ossifying fibroma and Adamantinoma, Giant cell tumor, Fibrous dysplasia, Ewing's Sarcoma, Eosinophilic Granuloma, Osteosarcoma, Chondroma, Chondrosarcoma, Malignant Fibrous Histiocytoma, and Metastatic Carcinoma.

Leukaemias refers to cancers of the white blood cells which are produced by the bone marrow. This includes but are not limited to the four main types of leukaemia; acute lymphoblastic (ALL), acute myeloblastic (AML), chronic lymphocytic (CLL) and chronic myeloid (CML).

In one embodiment, the invention relates to methods of treating viral infections, allergic diseases, autoimmune diseases and cancer as listed above, the method comprising the administration of an effective amount of a peptide of the present invention to a patient in need thereof.

In one embodiment, the present invention relates to the use of a peptide of the present invention for the manufacture of a medicament for the treatment of viral infections, allergic diseases, autoimmune diseases and cancer as listed above.

It is well-known in the art that cancer treatment regimes often include more than one medicament or treatment modality. In one embodiment, the present invention therefore provides a method for the treatment of cancer, the method comprising the administration of an effective amount of a peptide of the present invention in combination with an effective amounts of one or more of the following I through VI. In the present invention, 'in combination with' means that a peptide of the invention is administered (i) before, (ii) at the same time and/or (iii) after treatment with one or more of the following I through VI.

I. Agents that Induce Tumour Cell Death or Death of Virus-Infected Cells
    a) conventional chemotherapy
    b) radiation therapy
    c) monoclonal antibodies
    d) cell cycle control/apoptosis regulators
    e) growth factor and signal transduction modulators
    f) inhibitors of tumour vascularisation (angiogenesis inhibitors, anti-angiogenesis drugs)
    g) viral targeting (the use of a recombinant virus to destroy tumour cells)
    h) anti-viral agents
    i) hormonal agents II. Agents that Enhance the Immune Response Against Tumour Cells or Virus-Infected Cells
    j) immune system activators
    k) immune system inhibitors (e.g. agents that inhibit immune signals down-regulating the immune response), including anti-anergic agents
    l) therapeutic vaccines III. Agents that Interfere with Tumour Growth, Metastasis or Spread of Virus-Infected Cells
    m) integrins, cell adhesion molecules modulators
    n) anti-metastatics
    o) endothelial cell modulators IV. Internal Vaccination.

V. Tissue Factor Antagonist and Other Factors Influencing the Coagulation Cascade
    p) anti Factor Xa, anti Factor IIa inhibitors, anti-fibrinogenic agents
    q) pentasaccharides etc.

VI. Immunosuppressive/Immunomodulatory Agents
    r) agents with influence on T-lymphocyte homing e.g. FTY-720
    s) calcineurin inhibitors
    t) TOR inhibitors A more detailed description of some of the possible combination drugs is provided below I: Agents that Induce Tumour Cell Death or Death of Virus-Infected Cells a) Conventional Chemotherapeutic Agents In one embodiment of the invention, combination therapy is performed by administering a peptide of the present invention and conventional chemotherapic agents. Chemotherapeutic agents have different modes of actions such as by influencing either
    a) DNA level
    b) RNA level Non-limiting examples of conventional chemotherapeutic agents at the DNA level or on the RNA level are anti-metabolites (such as Azathioprine, Cytarabine, Fludarabine phosphate, Fludarabine, Gemcitabine, cytarabine, Cladribine, Capecitabine 6-mercaptopurine, 6-thioguanine, methotrexate, 5-fluorouracil, and hydroxyurea) alkylating agents (such as Melphalan, Busulfan, Cis-platin, Carboplatin, Cyclophosphamide, Ifosphamide, Dacarbazine, procarbazine, Chlorambucil, Thiotepa, Lomustine, Temozolamide) antimitotic agents (such as Vinorelbine, Vincristine, Vinblastine, Docetaxel, Paclitaxel) topoisomerase inhibitors (such as Doxorubicin, Amsacrine, Irinotecan, Daunorubicin, Epirubicin, Mitomycin, Mitoxantrone, Idarubicin, Teniposide, Etoposide, Topotecan) antibiotics (such as actinomycin and bleomycin) asparaginase, or the anthracyclines or the taxanes.

In one embodiment of the invention, combination therapy is performed by administering a peptide of the present invention and dacarbazine (DTIC).

b) Radiotherapy:

Certain tumors can be treated with radiation or radiopharmaceuticals. The source of radiation can be either external or internal to the patient being treated. When the source is external to the patient the therapy is known as external beam radiation therapy (EBRT). When the source of radiation is internal to the patient, the treatment is called brachytherapy (BT). Typical radioactive atoms that have been used include radium, Cesium-137, Iridium-192, Americium-241, Gold-198, Cobalt-57, Copper-67, Technetium-99, Iodide-123, Iodide-131 and Indium-111.

Radiation therapy is standard treatment to control unresectable or inoperable tumours and/or tumour metastases. Improved results have been seen when a radiation therapy has been combined with other therapies.

In an embodiment of the invention, a peptide of the present invention is administered in combination with radiation therapy.

c) Monoclonal Antibodies (Monoclonals; MAbs)

MAbs have been developed for the treatment of leukaemia and lymphoma as well as solid tumour, and this principle is gaining increasing interest. These antibodies work either by inhibiting functions that are vital for survival of the tumor cells, by delivering a toxic payload, by interrupting key signalling events, or by induction of antibody-dependent cell-mediated cytotoxicity (ADCC) or complement-directed cytotoxicity (CDC) against the tumor cells. Death of the tumor cells might then lead to the release of tumor antigens that "vaccinates" the immune system and stimulates it to produce a secondary response that then targets the tumor cell (i.e. 'internal vaccination' as described below). Over-expressed oncogenes and tumor-specific antigens are key targets for many mAbs under development.

Tumor antigens are described for example in Stauss H, Kawakami Y and Parmiani G: Tumor antigens recognized by T cells and antibodies. Taylor and Frances (2003). The invention covers antibodies raised against these targets. The invention also covers antibodies raised against viral antigens.

In an embodiment of the invention a peptide of the present invention is combined with the antibodies such as Rituximab, Alemtuzumab, Trastuzumab, Gemtuzumab, Gemtuzumab-ozogamicin (Myelotarg®, Wyeth) Cetuximab (Erbitux™), Bevacizumab, HuMax-CD20, HuMax-EGFr, Zamyl and Pertuzumab.

In an embodiment of the invention a peptide of the present invention is combined with Rituximab.

In an embodiment of the invention a peptide of the present invention is combined with Cetuximab.

In an embodiment of the invention a peptide of the present invention is combined with Bevacizumab.

In an embodiment of the invention a peptide of the present invention is combined with Bevacizumab and Cetuximab.

In an embodiment of the invention a peptide of the present invention is combined with Bevacizumab and Cetuximab.

In an embodiment of the invention a peptide of the present invention is combined with Panitumumab.

In an embodiment of the invention a peptide of the present invention is combined with Bevacizumab and Panitumumab.

In an embodiment of the invention a peptide of the present invention is combined with an antibody against tissue factor, killer Ig-like receptors (KIR), laminin-5, EGF-R, VEGF-R, PDGF-R, HER-2/neu, or an antibody against a tumor antigen such as PSA, PSCA, CEA, CA125, KSA, etc.

In an embodiment of the invention, a peptide of the present invention is administered together with a therapeutic antibody, such as those mentioned above, and further combined with additional ADCC-enhancing compounds, ex. blocking anti-KIR antibodies, NKG2D agonists, NKG2A antagonists, IL-2, IL-12, IL-15, IL-18 or IL-21.

In another embodiment of the invention a peptide of the present invention is administered as a combination with antibodies against viral antigens.

d) Cell Cycle Control/Apoptosis Regulators

A series of regulators are involved in the maintenance of normal cell-cycle. Compounds, which target regulators such as (i) cdc-25 (with NSC 663284 as a non-limiting example (Pu et al (2003) J Biol Chem 278, 46877)), (ii) cyclin-dependent kinases that overstimulate the cell cycle (with the following non-limiting examples: flavopiridol (L868275, HMR1275; Aventis), 7-hydroxystaurosporine (UCN-01, KW-2401; Kyowa Hakko Kogyo) and roscovitine (R-roscovitine, CYC202; Cyclacel)—as reviewed by Fischer & Gianella-Borradori (2003) Exp Op Invest Drugs 12, 955-970), and (iii) telomerase, the enzyme that helps cancer cells rebuild its telomeres are within the present invention such as the following non-limiting examples BIBR1532 (Damm et al (2001) EMBO J. 20, 6958-6968) and SOT-095 (Tauchi et al (2003) Oncogene 22, 5338-5347). Furthermore, drugs that interfere with apoptotic pathways are within the present invention, such as the following non-limiting examples: TNF-related apoptosis-inducing ligand (TRAIL)/apoptosis-2 ligand (Apo-2L), antibodies that activate TRAIL receptors, IFN-α and anti-sense Bcl-2. (see Igney and Krammer (2002) Nature Rev. Cancer 2, 277-288; Makin and Dive (2003) Trends Mol Med 9, 2519; Smyth et al (2003) Immunity 18, 1-6; Panaretakis et al (2003) Oncogene 22, 4543-4556 and references therein). In one embodiment of the invention A peptide of the present invention, is combined with one or more cell-cycle regulators and/or apoptosis-inducing agents.

In an embodiment of the invention above the compounds are selected from the group comprising cdc-25, NSC 663284, flavopiridol, 7-hydroxystaurosporine, roscovitine, BIBR1532 SOT-095, TNF-related apoptosis-inducing ligand (TRAIL)/apoptosis-2 ligand (Apo-2L), antibodies that activate TRAIL receptors, IFN-α and anti-sense Bcl-2.

e) Growth Factor Inhibitors

A number of mAbs against growth factors and growth factor receptors are being developed for the treatment of cancer. Thus, as a non-limiting example, members of the epidermal growth factor receptor (EGF-R) family are abnormally activated in many epithelial tumors, which often correlate with more aggressive clinical course. Antibodies directed against the extracellular ligand binding domain of these receptors and low molecular weight molecules that inhibit their tyrosine kinase domains are in late-stage clinical development or approved for treatment of cancer either as single agents or in combination with other cancer drugs. Non-limiting examples are Herceptin (monoclonal antibody), cetuximab (monoclonal antibody), Tarceva (low molecular weight inhibitor), and Iressa (low molecular weight inhibitor). In addition, the ligand can be neutralised before binding to the receptor.

In one embodiment of the invention a peptide of the present invention is combined with growth factor inhibitors.

In an embodiment of the invention the growth factor inhibitors are selected from the group comprising Herceptin (monoclonal antibody), cetuximab (monoclonal antibody), Tarceva (low molecular weight inhibitor), and Iressa (low molecular weight inhibitor).

In an embodiment of the invention a peptide of the present invention is combined with Herceptin.

f) Inhibitors of Tumor Vascularisation (Anti-Angiogenesis Drugs and Anti-Metastatic Agents)

Tumor growth is dependent on sufficient blood supply and hence development of new blood vessels. This general feature of solid tumors seems attractive from a therapeutic point of view, i.e. reduced tumor growth and tumor regression is expected when treating patients with cancer with anti-angionesis drugs. Currently. more than 60 anti-angionesis drugs are in clinical trials including the natural occurring endostatin and angiostatin (reviewed in Marx (2003) Science 301, 452-454). But also older chemotherapy drugs, other medicines and radiation therapy have anti-angiogenic effects. In one type of embodiments of the present invention is combination therapy with IL-21, analogues or derivatives thereof and one or more anti-angiogenic agents, such as the following non-limiting examples endostatin, angiostatin, antibodies that block factors that initiate angiogenesis (e.g. anti-VEGF-Avastin), low molecular compounds that inhibit angiogenesis by inhibiting key elements in relevant signal transduction pathways.

Attacking the vasculature of the tumor and the extracellular matrix has attracted increasing awareness. The following principles have so far been developed: Blockage of the endothelial cell, administration of angiostatin and endostatin, VEGF targeting and extracellular matrix In an embodiment of the invention a peptide of the present invention is combined with an anti-angiogenesis drug.

In an embodiment of the invention the anti-angiogenesis drug is selected from the group comprising: avastin, neovastat, thalidomide, PTK787, ZK222584, ZD-6474, SU6668, PD547,632, VEGF-Trap, CEP-7055, NM-3, SU11248. g) Viral targeting Viral targeting uses a recombinant virus—usually replication incompetent—to destroy a tumor directly. In practice, at least one round of replication occurs before the virus is incapacitated. Hence, the tumor is lysed, which often leads to systemic immunization with resulting protection. This approach has been refined further using genetic modification to enhance the immune response. For example, the genetic insertion of a human GM-CSF gene into a herpes simplex virus type 2 vector has been used improve the efficacy of the vaccine. In one embodiment of the invention, combination therapy is performed by administering IL-21, an analogue or a derivative thereof and viral targeting.

i) Hormonal Agents.

Hormonal agents are primarily know in the treatment of hormonal dependent cancers such as ovarian cancer, breast cancer and prostate cancer such as anti-androgen and anti-oestrogen therapy. Hormones and anti-hormones are compoundssuch as Estramustine phosphate, Polyestradiol phosphate, Estradiol, Anastrozole, Exemestane, Letrozole, Tamoxifen, Megestrol acetate, Medroxyprogesterone acetate, Octreotide, Cyproterone acetate, Bicaltumide, Flutamide, Tritorelin, Leuprorelin, Buserelin or Goserelin.

In an embodiment of the invention a peptide of the present invention is combined with hormone therapy.

II: Agents that Enhance the Immune Response Against Tumor Cells or Virus-Infected Cells
j) Immune System Activators The following list of components or agents that can be used together with a peptide of the present invention in combination therapy of cancer and viral infections by enhancing the efficacy of the immune system is not intended in any way to limit the scope of the invention:

Adjuvants:

Immunotherapy consist of specific and non-specific modalities. As examples of non-specific immunotherapy are adjuvants acting primarily as catalyst for the initiation of an immune response. Non-limiting examples of such vaccine adjuvants are QS21, GM-CSF and CpG oligodeoxynucleotides, lipopolysaccharide and polyinosinic:polycytidylic acid.

In one embodiment of the invention a peptide of the present invention is combined with one or more adjuvants.

In an embodiment of the invention the adjuvants are selected from the group comprising: QS21, GM-CSF and CpG oligodeoxynucleotides, lipopolysaccharide and polyinosinic:polycytidylic acid, a-Galctosylceramide or analogues thereof, histamine dihydrochloride, or aluminum hydroxide.

Cytokines:

Non-limiting examples of cytokines are IFN-α, IFN-β IFN-γ, IL-2, PEG-IL-2, IL-4, IL-6, IL-7, IL-12, IL-13, IL-15, IL-18, IL-21, IL-23, IL-27, IL-28a, IL-28b, IL-29, GM-CSF, Flt3 ligand or stem cell factor.

In an embodiment of the invention a peptide of the present invention is combined with one or more cytokines.

In an embodiment of the invention an IL-21 is combined with one or more of the compounds selected from the group comprising: IFN-α, IFN-β, IFN-γ, IL-2, PEG-IL-2, IL-4, IL-6, IL-7, IL-12, IL-13, IL-15, IL-18, IL-21, IL-23, IL-27, IL-28a, IL-28b, IL-29, GM-CSF, Flt3 ligand or stem cell factor, or an analogue or derivative of any of these.

In an embodiment of the invention, the compounds are selected from the group comprising: IFN-α, IFN-β, IFN-γ, PEG-IL-2, IL-18, IL-23, IL-27, IL-28a, IL-28b, IL-29.

In an embodiment of the invention a peptide of the present invention is combined with one of the following: IL-2, PEG-IL-2, IL-7, IL-12, IL-15, IL-18 and IFN-α.

In an embodiment of the invention a peptide of the present invention is combined with IL-12 In an embodiment of the invention a peptide of the present invention is combined with IFN-α.

In an embodiment of the invention a peptide of the present invention is combined with PEG-IL-2, In an embodiment of the invention a peptide of the present invention is combined with more than one of the following: IL-2, PEG-IL-2, IL-7, IL-12, IL-15, IL-18 and IFN-α. In an embodiment of the invention a peptide of the present invention is combined with at least one of the following: IL-2, PEG-IL-2, IL-7, IL-12, IL-15, IL-18 and IFN-α and one additional active component. In an embodiment of the invention a peptide of the present invention is combined with at least one of the following: IL-2, PEG-IL-2, IL-7, IL-12, IL-15, IL-18 and IFN-α and one additional cytokine from the list above. In an embodiment of the invention a peptide of the present invention is combined with IFN-α and GM-CSF. In an embodiment of the invention a peptide of the present invention is combined with IFN-α and thymopentin.

In an embodiment of the invention a peptide of the present invention is combined with IFN-γ.

In an embodiment of the invention a peptide of the present invention is combined with autologous TILs and IFN-α.

In an embodiment of the invention a peptide of the present invention is combined with IFN-α and IL-12.

In an embodiment of the invention a peptide of the present invention is combined with Cis-platin and IFN-α.

In an embodiment of the invention a peptide of the present invention is combined with Cis-platin, tamoxifen and IFN-α.

In an embodiment of the invention a peptide of the present invention is combined with Cis-platin, DTIC, tamoxifen and IFN-α.

In an embodiment of the invention a peptide of the present invention is combined with Cis-platin, DTIC, tamoxifen and GM-CSF.

In an embodiment of the invention a peptide of the present invention is combined with Cis-platin, Carmustine, DTIC and IFN-α.

In an embodiment of the invention a peptide of the present invention is combined with Cis-platin, Carmustine, DTIC, tamoxifen and IFN-α.

In an embodiment of the invention a peptide of the present invention is combined with Cis-platin, Carmustine, DTIC, carboplatin, tamoxifen and IFN-α.

In an embodiment of the invention a peptide of the present invention is combined with Cis-platin, DTIC, Vinblastine, tamoxifen and IFN-α.

In an embodiment of the invention a peptide of the present invention is combined with Cis-platin, Vinblastine, temozolomide and IFN-α.

In an embodiment of the invention a peptide of the present invention is combined with Cis-platin, Carmustine, DTIC, Vindesine, tamoxifen and IFN-α.

In an embodiment of the invention a peptide of the present invention is combined with Cis-platin, tamoxifen and IFN-α.

In an embodiment of the invention a peptide of the present invention is combined with Cis-platin, Vinblastine, DTIC and IFN-α.

In an embodiment of the invention a peptide of the present invention is combined with DTIC and IFN-α.

In an embodiment of the invention a peptide of the present invention is combined with DTIC, GM-CSF and IFN-α.

In an embodiment of the invention a peptide of the present invention is combined with DTIC, thymosin-α and IFN-α.

In an embodiment of the invention a peptide of the present invention is combined with Vinblastine and IFN-α.

In an embodiment of the invention a peptide of the present invention is combined with 5-fluorouracil and IFN-α.

In an embodiment of the invention a peptide of the present invention is combined with Fotemustine and IFN-α.

In an embodiment of the invention a peptide of the present invention is combined with Oxaliplatin and IFN-α.

In an embodiment of the invention a peptide of the present invention is combined with Oxaliplatin, tamoxifen and IFN-α.

In an embodiment of the invention a peptide of the present invention is combined with Oxaliplatin, DTIC, tamoxifen and IFN-α.

In an embodiment of the invention a peptide of the present invention is combined with Oxaliplatin, DTIC, tamoxifen and GM-CSF.

In an embodiment of the invention a peptide of the present invention is combined with Oxaliplatin, Carmustine, DTIC and IFN-α.

In an embodiment of the invention a peptide of the present invention is combined with Oxaliplatin, Carmustine, DTIC, tamoxifen and IFN-α.

In an embodiment of the invention a peptide of the present invention is combined with Oxaliplatin, Carmustine, DTIC, carboplatin, tamoxifen and IFN-α.

In an embodiment of the invention a peptide of the present invention is combined with Oxaliplatin, DTIC, Vinblastine, tamoxifen and IFN-α.

In an embodiment of the invention a peptide of the present invention is combined with Oxaliplatin, Vinblastine, temozolomide and IFN-α.

In an embodiment of the invention a peptide of the present invention is combined with Oxaliplatin, Carmustine, DTIC, Vindesine, tamoxifen and IFN-α.

In an embodiment of the invention a peptide of the present invention is combined with Oxaliplatin, tamoxifen and IFN-α.

In an embodiment of the invention a peptide of the present invention is combined with Oxaliplatin, Vinblastine, DTIC and IFN-α.

In an embodiment of the invention a peptide of the present invention is combined with 5-fluorouracil or an orally active analogue thereof.

In an embodiment of the invention a peptide of the present invention is combined with oxaliplatin and 5-fluorouracil or an orally active analogue thereof.

In an embodiment of the invention a peptide of the present invention is combined with oxaliplatin, leucovorin, and 5-fluorouracil or an orally active analogue thereof.

In an embodiment of the invention a peptide of the present invention is combined with Irinotecan.

In an embodiment of the invention a peptide of the present invention is combined with Irinotecan and oxaliplatin.

In an embodiment of the invention a peptide of the present invention is combined with Irinotecan and Cetuximab.

In an embodiment of the invention a peptide of the present invention is combined with Irinotecan and bevacizumab.

In an embodiment of the invention a peptide of the present invention is combined with Irinotecan and Cetuximab and bevacizumab.

In an embodiment of the invention a peptide of the present invention is combined with DTIC and autologous LAK cells.

In an embodiment of the invention a peptide of the present invention is combined with Gemcitabine and IFN-α.

Any of the above combinations can be further combined with IL-2.

Cellular Immunotherapy

Examples of cellular immunotherapy (or adoptive immunotherapy) include re-infusion of ex-vivo expanded tumor infiltrating T cells or genetically modified T cells.

In one embodiment of the invention, combination therapy is combining administration of a peptide of the present invention and cellular immunotherapy.

Cellular immunotherapy may include isolation of cells that can stimulate or exert an anti-cancer response from patients, expanding these into larger numbers, and reintroducing them into the same or another patient. In one aspect this may be CD4$^+$ or CD8$^+$ T cells recognizing tumor specific antigens or tumor-associated antigens. In another aspect this may be B cells expressing antibodies specific for tumor specific antigens or tumor-associated antigens. In another aspect this may be NK cells that are able to kill the tumor cells. In a preferred aspect this may be dendritic cells (DC) that are cultured ex vivo with a DC-expanding agent (e.g. GM-CSF or Flt3-L), loaded with tumor specific antigens or tumor-associated antigens and re-infused into a patient in need thereof. In one embodiment of the invention, combination therapy is combining administration of A peptide of the present invention, and cellular immunotherapy or adoptive therapy.

In an embodiment of the invention the cell adoptive therapy comprises CD4$^+$ or CD8$^+$ T cells recognizing tumor specific antigens or tumor-associated antigens.

In an embodiment of the invention the cell adoptive therapy comprises B cell expressing antibodies specific for tumor specific antigens or tumor-associated antigens.

In an embodiment of the invention cell adoptive therapy comprises NK cells that are able to kill the tumor cells.

In an embodiment of the invention cell adoptive therapy comprises dendritic cells (DC).

In an embodiment of the above the dendritic cells are cultured in vivo with a DC expanding agent (e.g. GM-CSF or Flt3-L), loaded with tumor specific antigens or tumor-associated antigens and reintroduced in vivo.

k) Agents that Block Inhibitory Signalling in the Immune System.

Immune responses, including anti-tumor and anti-viral responses, are regulated by a balance of signalling via stimulatory and inhibitory receptors in cells of the immune system. A shift towards abundant signalling via activatory receptors may lead to more effective immune responses, whereas enhanced signalling via inhibitory receptors may lead to less productive responses, or even may impair immunity. In order to enhance anti-tumor or anti-viral responses, it is useful to therapeutically block signalling via inhibitory receptors, in order to shift the balance towards activation. Therefore, agents that block inhibitory receptors, or inhibitory signalling pathways, are preferred agents for combination treatment, in conjunction with the a peptide of the present invention. Non-limiting examples of such agents that block inhibitory receptors are mAbs specific for CTLA-4 (anti-CTLA-4), mAbs specific for KIR (anti-KIR), mAbs specific for LIR (anti-LIR), mAbs specific for CD94 (anti-CD94), or mAbs specific for NKG2A (anti-NKG2A).

Anti-allergic agents are small compounds, proteins, glycoproteins or antibodies that can break tolerance to tumor and cancer antigens.

Although the presence of tumor infiltrating lymphocytes (TILs) correlates with improved clinical outcome in a number of different cancer forms, there is clearly a need to improve the activity of these TILs due to anergy or tolerance to tumor antigens. The anergic condition may in a substantial number of cases be counteracted by monoclonal antibodies that prevent CTLA-4-induced anergy or tolerance. Blockade of CTLA-4 has been shown in animal models, and in human cancer patients, to improve the effectiveness of cancer therapy suggesting that CTLA-4 blockade can be used to break the tolerance to cancer and tumor antigens. A non-limiting example of a monoclonal antibody that may be used for induction of the activity of TILs is MDX-010 (Phan et al. (2003) Proc. Natl. Acad. Sci. U.S.A. 100: 8372).

In one embodiment of the invention, combination therapy is performed by administering a peptide of the present invention and one or more agents that break the tolerance to cancer, tumor or viral antigens. In an embodiment of the invention a peptide of the present invention is combined with MDX-010.

In an embodiment of the invention a peptide of the present invention is combined with antibodies against CTLA-4.

In an embodiment of the invention a peptide of the present invention is combined with antibodies against KIR.

In an embodiment of the invention a peptide of the present invention is combined with antibodies against CD94.

In an embodiment of the invention a peptide of the present invention is combined with antibodies against NKG2A.

In an embodiment of the invention a peptide of the present invention is combined with antibodies against an inhibitory receptor expressed on an NK cell, a T cell or a NKT cell.

In an embodiment of the invention a peptide of the present invention is combined with an antagonist of an inhibitory receptor.

In an embodiment of the invention a peptide of the present invention is combined with an antagonist of a signalling protein involved in transmission of inhibitory signals.

l) Therapeutic Vaccines

The development of almost all human cancers involves genetic alterations, and this may lead to expression of altered molecules in tumor cells and over-expression of normal molecules, respectively. In principle, these changes should lead to an immune response from the host (immune surveillance). Obviously, this theoretical activation of the immune system only leads to spontaneous regression of the tumor in very few, exceptional cases. This may, among other factors, be due to lack of "danger signals", a phenomenon that has attracted increasing interest.

Tumour specific antigens have been identified, and vaccination with such antigens may stimulate the immune system to eradicate the tumor. Tumor-specific antigens (TSAs) are a relatively small group of antigens exemplified by the cancer-testis antigens. These genes are silent in normal tissue but are expressed by cancerous cells. They are highly specific markers of disease and include MAGE (melanoma antigen gene) found in melanoma.

Tumor-associated antigens (TAAs) are usually differentiation antigens expressed by normal cells but massively over-expressed in cancerous tissue. Targets initially thought to be specific for a particular cancer are actually quite common in many tumors, such as the gangliosides and mucin antigens. Classical differentiation antigens include MART-1 (melanoma antigen recognized by T cells) and gp 100, both from melanoma, tyrosinase, carcinoembryonic antigen (CEA) and gp75.

Mutational antigens: Point mutations are common in many cancers, and often occur in a similar location, such as the common mutation of the P53 or ras oncogenes. In vitro induction of human cytotoxic T-lymphocyte (CTL) responses against peptides of mutant and wild-type p53 has been reported. In a mouse model, mutant p53-pulsed dendritic cells were able to induce p53 specific CTL and inhibit the growth of established tumors.

Viral antigens: Certain viruses are oncogenic and gene products encoded by these viruses can elicit immune responses and thus serve as cancer antigens. An example is the E6 and E7 proteins from human papilloma virus type 16, which have been shown to induce cytotoxic T-lymphocyte responses in vitro.

Tumor-specific antigens, tumor-associated antigens and/or mutational antigens and viral antigens may be used either as peptides, recombinant purified single-agent antigens, combinations of recombinant purified antigens and/or purified or pools of antigens isolated from cancer cells or tumor cells as a vaccine to elicit an anti-tumor immune response. Similarly, peptides, recombinant purified single-agent antigens, combinations of recombinant antigens and/or purified or pools of antigens isolated from virus-infected cells may be used in a vaccine to elicit a response against virus-infected cells. Therapeutic vaccines can also be in the form of autologous tumor cell lysates or extracts, or lysates or extracts of allogeneic tumor cell-lines. Therapeutic vaccines can also be in the form of a DNA vaccine to elicit immune response against cancer and virus-infected cells. Said DNA vaccine may consist of an expression vector encoding the antigen alone or encoding the antigen together with a cytokine (eg. GM-CSF, IL-2, IL-12 or IL-21) that may enhance the immune response against cancer and virus-infected cells. Said DNA vaccine may also consist of a modified virus (eg. Fowlpox virus, Vaccinia virus or Adenovirus) that contains a DNA sequence encoding the antigen alone or encoding the antigen together with a cytokine. Therapeutic vaccines can also be in the form of anti-idiotype antibodies to elicit immune response against cancer and virus-infected cells. Therapeutic vaccines can also be in the form of autologous dendritic cells loaded with said antigens or peptides derived thereof together with a DC modifying agent, such as cytokines, toll-like receptor (TLR) agonists, CpG oligodeoxynucleotides, GM-CSF, or heat-shock proteins.

Said vaccine-mediated elicitation of an anti-tumor response or a response against virus-infected cells may be enhanced by administering adjuvants, cytokines, toll-like receptor (TLR) agonists, CpG oligodeoxynucleotides, dendritic cells, GM-CSF, or heat-shock proteins. In one embodiment of the invention, combination therapy is performed by administering A peptide of the present invention with one or more therapeutic vaccines with or without adjuvants, cytokines, toll-like receptor (TLR) agonists, CpG oligodeoxynucleotides, dendritic cells, GM-CSF, or heat-shock proteins.

n) Antimetastatics

Metastatic cancer cells penetrate the extracellular matrix (ECM) and the basement membrane of the blood vessels to metastasise to a target organ (ectopic site). EMC consists of proteins embedded in a carbohydrate complex (heparan sulfate peptidoglycans), and proteases surrounding the tumour are active in this breaking down the host tissue. Anti-metastatic agents antagonise the effect of such proteases (e.g. metalloproteinase inhibitors) (Coussens et al. Science 2002; 295:2387-2392). In an embodiment of the present invention is combination therapy with a peptide of the present invention and one or more anti-metastatic agents, such as metalloproteinase inhibitors.

IV: Internal Vaccination

"Internal vaccination" and "internal vaccination therapy" refer to drug- or radiation-induced cell death of tumor cells that leads to elicitation of an immune response directed towards (i) said tumor cells as a whole or (ii) parts of said tumor cells including (a) secreted proteins, glycoproteins or other products, (b) membrane-associated proteins or glycoproteins or other components associated with or inserted in membranes and (c) intracellular proteins or other intracellular components. The immune response may be humoral (i.e. antibody—complement-mediated) or cell-mediated including but not limited to development of cytotoxic T lymhocytes that recognized said tumor cells or parts thereof. Internal vaccination bears many similarities to other vaccination procedures and involves many or all of the same cellular components of the hematopoietic and immune system with the advantage that the immunogens or antigenic components are endogenous and thus representative for the antigenic repertoire of said tumor cells. Internal vaccination may thus be considered personalized vaccination, which is elicited by use of general procedures for cancer treatment leading to tumor cell death. In addition to radiotherapy, non-limiting examples of drugs and agents that can be used to induce said tumor cell-death and internal vaccination are conventional chemotherapeutic agents, cell-cycle inhibitors, anti-angiogenesis drugs, monoclonal antibodies, apoptosis-inducing agents and signal transduction inhibitors.

"Peptide of the present invention and internal vaccination combination therapy" refers to combination therapy where a peptide of the present invention is administered to patients with cancer who are treated with internal vaccination. A peptide of the present invention may be administered prior to, concomitant with or after performing internal vaccination.

In an embodiment of the invention a peptide of the present invention is included in an internal vaccination therapy.

Gene therapy includes transfer of genetic material into a cell to transiently or permanently alter the cellular phenotype. Different methods are investigated for delivery of cytokines, tumor antigens and additional stimulatory molecules. In the context of this invention, a peptide of the present invention may be either the delivered agent or co-administered. In an embodiment of this invention, a peptide of the present invention may be administered as a polynucleotide. The polynucleotide is described in WO 00/53761.

VI: Immunosuppressive/Immunomodulatory Agents r) Agents with Influence on T-Lymphocyte Homing e.g. FTY-720 s) Calcineurin Inhibitors

Calcineurin inhibitors such as valspodar, PSC 833, are active in preventing resistance development to cytotoxic agents due to inhibitory effects on MDR-1 and p-glycoprotein.

t) TOR-Inhibitors

TOR-inhibitors act by blocking the serine-threonine kinase mammalian TOR (mTOR). Compounds such as sirolimus, everolimus and rapmycin are antiproliferative agents. They are involved in the downstream signaling cascades and are therefore relevant in the treatment of all tumour types (eg antiangiogenic properties).

In one embodiment, the above mentioned cancer treatment modalities are combined with SEQ ID No: 2 in the same way as exemplified for a peptide of the present invention. In one embodiment, the present invention provides pharmaceutical compositions as discussed below comprising a peptide with SEQ ID No: 2 and one or more of the cancer treatment modalities as described above.

Pharmaceutical Compositions

Another object of the present invention is to provide a pharmaceutical formulation comprising a peptide of the present invention which is present in a concentration from $10^{-15}$ mg/ml to 200 mg/ml, such as $10^{-10}$ mg/ml-5 mg/ml, and wherein said formulation has a pH from 2.0 to 10.0. Optionally, said formulation may comprise one or more further cancer agents as described above. The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a peptide of the present invention, and a buffer, wherein said OGP protein is present in a concentration from 0.1-100 mg/ml, and wherein said formulation has a pH from about 2.0 to about 10.0.

In a another embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 20$^{th}$ edition, 2000.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 20$^{th}$ edition, 2000.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 20$^{th}$ edition, 2000.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 20$^{th}$ edition, 2000.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or mixtures thereof) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or mixtures thereof) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fafty acids and salts thereof $C_6$-$C_{12}$ (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 20$^{th}$ edition, 2000.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a peptide of the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the peptide of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of a peptide of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and super-critical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the peptide of the present invention in the form of a nasal or pulmonal spray. As a still further option, the pharmaceutical compositions containing the peptide of the present invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahem. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the peptide of the present invention is stable for more than 6 weeks of usage and for more than 3 years of storage.

In another embodiment of the invention the pharmaceutical formulation comprising the peptide of the present invention is stable for more than 4 weeks of usage and for more than 3 years of storage.

In a further embodiment of the invention the pharmaceutical formulation comprising the peptide of the present invention is stable for more than 4 weeks of usage and for more than two years of storage.

In an even further embodiment of the invention the pharmaceutical formulation comprising the peptide of the present invention is stable for more than 2 weeks of usage and for more than two years of storage.

EXAMPLES

Activity Test of IL-21 Variants hIL-21 wild type and mutant proteins were analyzed using in a cellular activity assay using a stat-regulated luciferase reporter system.

The assay employs the murine Baf3 cell line, which has been stably transfected to express the human IL-21R and a Stat-linked luciferase reporter construct. The Baf3 cells expresses endogenously the gamma C 'common chain' which constitutes an essential component of the signalling IL-21 receptor complex. The Baf3/hIL-21R reporter cell line was starved in IL-3 free medium for 6 hours prior to stimulation. A dosis-response analysis was subsequently carried out using stimulation of the cells for 24 hours.

FIG. 1 represents an analysis of proteins expressed transiently in HEK293 FS cells (Stengaard-Pedersen et al. N. Engl. J. Med. (2003) 349: 554; Invitrogen). The proteins were analyzed in the form of raw supernatants harvested 48 hours post transfection.

FIG. 2 represents an analysis of wild type and mutant hIL-21 proteins analyzed as purified proteins. Chim-IL21 is the IL-21 sub[K77-T92] (SEQ ID No.7). Here constructs were prepared for expression in *E. coli* and purified through refolding of proteins present in inclusion bodies.
Alternative Activity Test of IL-21 Variants The cDNAs encoding the IL-21 variants are analyzed by transient expression followed by activity analysis in a stat-regulated reporter system.

The cDNAs are transfected into HEK293 FreeStyle cells (Stengaard-Pedersen et al. N. Engl. J. Med. (2003) 349: 554; Invitrogen). Supernatants are collected from serum-free medium at 48 hours post transfection and analyzed in a cellular bioassay. The assay em-ploys the murine Baf3 cell line, stably transfected to express the human IL-21R and a Stat-linked luciferase reporter construct. The Baf3 cells expresses endogenously the γc component of the active IL-21 receptor complex. The Baf3/hIL-21R reporter cell line is starved in IL-3 free medium for 18 hours prior to stimulation. A dosis-response analysis is carried out using raw supernatant from the HEK293-FS tranfectants. Duration of the stimulation is four hours.
Pharmacological Methods The following in vitro method is used to investigate enhancement of ADCC.

Target cells expressing the target antigen are incubated with the antibody against the target antigen and peripheral blood mononuclear cells, NK cells, neutrophils, macrophages, monocytes or DC as effector cells. Effector cells may be pre-incubated for 1 to 10 days with IL-21, or IL-21 may be added to the culture containing both effector and target cells. Other compounds that can enhance ADCC might be included in the culture or pre-incubation culture. Efficiency of ADCC will be measured as specific $^{51}$Cr release from the target cells or as LDH activity as described previously (Golay et al., *Haematologica* 88:1002-1012, 2003 or Liu et al., *Cancer Immun* 2:13, 2002 or Watanabe et al., *Breast Cancer Res Treat* 53:199-207, 1999).

Determination of ADCC using a flow cytometry based assay as described previously (Flieger et. al., *J Immunother* 23:480-486, 2000 or Flieger et al., *J Immunol Methods* 180: 1-13, 1995 or Flieger et al., *Hybridoma* 18:63-68, 1999).

Determination of ADCP through two-color fluorescence assay as described in Watanabe et al., *Breast Cancer Res Treat* 53:199-207, 1999 or Akewanlop et al., *Cancer Res* 61:4061-4065, 2001.

An in vivo method for determining the enhancement of ADCC is outlined below:

Leukaemia cells or transformed cells are injected i.v., i.p. or s.c. in syngeneic animals followed by treatment with the therapeutic antibody recognising an antigen expressed by the leukaemia cells or transformed cells, with or without IL-21 therapy. Endpoints are tumor burden and survival. The involvement of ADCC may be confirmed by the use of FcγRI blocking antibodies or by the use of FcγRI-deficient mice.

An in vivo method to investigate enhancement of ADCC towards target cells of human origin is described previously in Zhang et al., *Blood* 102:284-288, 2003 or Flavell et al. *Cancer Res* 58:5787-5794, 1998. According to these models human leukaemia cells or transformed cells are injected i.v., i.p. or s.c. in SCID mice followed by treatment with the therapeutic antibody recognising an antigen expressed by the leukaemia cells or transformed cells, with or without IL-21 therapy.

Tumor cell lines, e.g. Lewis Lung Carcinoma (LLC) cells or B16-F10 melanoma cells or renal renal cell carcinoma cells or 4T1 breast carcinoma cells are implanted s.c. in syngeneic mice. When the tumors become palpable, the mice are treated with IL-21 in combination with other anti-cancer agents as described in this application. The methodology is described in Palumbo et al., Cancer Res. 62:6966-6972 (2002); Bove et al., *Biochem Biophys Res Commun* 291: 1001-1005 (2002); Wigginton et al., *J Immunol* 169:4467-4474 (2002).

Tumor cell lines, e.g. Lewis Lung Carcinoma (LLC) cells or B16-F10 melanoma cells are implanted s.c. in syngeneic mice. The primary tumor is removed after 1-4 weeks, and the mice are treated with IL-21 in combination with other anti-cancer agents as described in this application. The methodology is described in Palumbo et al., Cancer Res. 62:6966-6972 (2002).

Tumor cell lines, e.g. Lewis Lung Carcinoma (LLC) cells or B16-F10 melanoma cells or renca renal cell carcinoma cells are injected i.v. in syngeneic mice and the mice are treated with IL-21 in combination with other anti-cancer agents as described in this application. The methodology is described in Amirkhosravi et al., *Thromb. Haemost.* 87:930-936 (2002); Hosaka et al., *Cancer Lett* 161:231-240 (2000); Maini et al., In vivo 17:119-123 (2003).

Renal renal cell carcinoma cells are injected intra-renally in one kidney in syngeneic mice. The primary tumor is removed after 1-4 weeks, and the mice are treated with IL-21 in combination with other anti-cancer agents as described in this application. The methodology is described in Murphy et al., *J Immunol* 170:2727-2733 (2003).

The invention claimed is:

1. An isolated variant human interleukin-21 (IL-21) peptide comprising an amino acid sequence which varies from SEQ ID NO:2 in that four to eight amino acids in the region of amino acid residues 71-92 of SEQ ID NO:2 can be deleted, and zero to ten conservative amino acid substitutions can occur in the region of amino acid residues 65-96 of SEQ ID NO:2, wherein the variant binds to the human IL-21 receptor.

2. The peptide of claim 1, wherein up to 8 of the amino acid residues in the region of the amino acid residues 83-90 of SEQ ID NO:2 are deleted or substituted.

3. The peptide of claim 1, wherein up to 6 of the amino acid residues in the region of the amino acid residues 83-88 of SEQ ID NO:2 are deleted or substituted.

4. The peptide of claim 1, wherein the amino acids acid residues in the region of the amino acid residues 83-86 of SEQ ID NO:2 are deleted or substituted.

5. The peptide of claim 1, wherein up to 7 of the amino acid residues in the region of the amino acid residues 82-88 of SEQ ID NO:2 are deleted or substituted.

6. The peptide of claim 1, wherein up to 10 of the amino acid residues in the region of the amino acid residues 71-92 of SEQ ID NO:2 are deleted or substituted.

7. The peptide of claim 1, wherein up to 10 of the amino acid residues in the region of the amino acid residues 77-92 of SEQ ID NO:2 are deleted or substituted.

8. The peptide of claim 1, wherein up to 10 of the amino acid residues in the region of the amino acid residues 77-96 of SEQ ID NO:2 are deleted or substituted.

9. The peptide of claim 1, wherein the peptide has the IL-21 activity that is at least the same level as that of the wild-type human IL-21 in an IL-21 receptor activity assay.

10. A pharmaceutical composition comprising the peptide according to claim 1 and a pharmaceutically acceptable carrier.

11. The peptide of claim 1, wherein the peptide comprises (A) the amino acid sequence of SEQ ID NO:3, or (B) the amino acid sequence of (A) further comprising an N-terminal Met residue.

12. The peptide of claim 1, wherein the peptide comprises (A) the amino acid sequence of SEQ ID NO:4, or (B) the amino acid sequence of (A) further comprising an N-terminal Met residue.

13. The peptide of claim 1, wherein the peptide comprises (A) the amino acid sequence of SEQ ID NO:5, or (B) the amino acid sequence of (A) further comprising an N-terminal Met residue.

14. The peptide of claim 1, wherein the peptide comprises (A) the amino acid sequence of SEQ ID NO:6, or (B) the amino acid sequence of (A) further comprising an N-terminal Met residue.

15. The peptide of claim 1, wherein the peptide comprises (A) the amino acid sequence of SEQ ID NO:7, or (B) the amino acid sequence of (A) further comprising an N-terminal Met residue.

16. The peptide of claim 1, wherein the peptide comprises (A) the amino acid sequence of SEQ ID NO:8, or (B) the amino acid sequence of (A) further comprising an N-terminal Met residue.

17. A pharmaceutical composition comprising the peptide according to any one of claims 11 and 12-16 and a pharmaceutically acceptable carrier.

* * * * *

SEQUENCE LISTING

<160> NUMBER OF SEQ ID NOS: 11

<210> SEQ ID NO 1
<211> LENGTH: 162
<212> TYPE: PRT
<213> ORGANISM: Homo sapiens

<400> SEQUENCE: 1

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
        50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 2
<211> LENGTH: 133
<212> TYPE: PRT
<213> ORGANISM: homo sapiens

<400> SEQUENCE: 2

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

```
<210> SEQ ID NO 3
<211> LENGTH: 129
<212> TYPE: PRT
<213> ORGANISM: Artificial
<220> FEATURE:
<223> OTHER INFORMATION: IL-21 variant

<400> SEQUENCE: 3

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Gln Lys His Arg Leu Thr Cys Pro Ser Cys Asp Ser Tyr Glu
                85                  90                  95

Lys Lys Pro Pro Lys Glu Phe Leu Glu Arg Phe Lys Ser Leu Leu Gln
            100                 105                 110

Lys Met Ile His Gln His Leu Ser Ser Arg Thr His Gly Ser Glu Asp
        115                 120                 125

Ser

<210> SEQ ID NO 4
<211> LENGTH: 127
<212> TYPE: PRT
<213> ORGANISM: Artificial
<220> FEATURE:
<223> OTHER INFORMATION: IL-21 variant

<400> SEQUENCE: 4

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn His Arg Leu Thr Cys Pro Ser Cys Asp Ser Tyr Glu Lys Lys
                85                  90                  95

Pro Pro Lys Glu Phe Leu Glu Arg Phe Lys Ser Leu Leu Gln Lys Met
            100                 105                 110

Ile His Gln His Leu Ser Ser Arg Thr His Gly Ser Glu Asp Ser
        115                 120                 125

<210> SEQ ID NO 5
<211> LENGTH: 125
<212> TYPE: PRT
<213> ORGANISM: Artificial
<220> FEATURE:
<223> OTHER INFORMATION: IL-21 variant
```

<400> SEQUENCE: 5

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Leu Thr Cys Pro Ser Cys Asp Ser Tyr Glu Lys Lys Pro Pro
                85                  90                  95

Lys Glu Phe Leu Glu Arg Phe Lys Ser Leu Leu Gln Lys Met Ile His
            100                 105                 110

Gln His Leu Ser Ser Arg Thr His Gly Ser Glu Asp Ser
        115                 120                 125

<210> SEQ ID NO 6
<211> LENGTH: 126
<212> TYPE: PRT
<213> ORGANISM: Artificial
<220> FEATURE:
<223> OTHER INFORMATION: IL-21 variant

<400> SEQUENCE: 6

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr His Arg Leu Thr Cys Pro Ser Cys Asp Ser Tyr Glu Lys Lys Pro
                85                  90                  95

Pro Lys Glu Phe Leu Glu Arg Phe Lys Ser Leu Leu Gln Lys Met Ile
            100                 105                 110

His Gln His Leu Ser Ser Arg Thr His Gly Ser Glu Asp Ser
        115                 120                 125

<210> SEQ ID NO 7
<211> LENGTH: 127
<212> TYPE: PRT
<213> ORGANISM: Artificial
<220> FEATURE:
<223> OTHER INFORMATION: IL-21 variant

<400> SEQUENCE: 7

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

```
Cys Phe Gln Lys Ala Gln Leu Lys Ser Ala Asn Thr Gly Asn Asn Glu
            50                  55                  60

Arg Ile Ile Asn Val Ser Ile Lys Lys Leu Lys Arg Asn Leu Trp Gly
 65                  70                  75                  80

Leu Ala Gly Leu Asn Ser Cys Pro Ser Cys Asp Ser Tyr Glu Lys Lys
                85                  90                  95

Pro Pro Lys Glu Phe Leu Glu Arg Phe Lys Ser Leu Leu Gln Lys Met
            100                 105                 110

Ile His Gln His Leu Ser Ser Arg Thr His Gly Ser Glu Asp Ser
            115                 120                 125

<210> SEQ ID NO 8
<211> LENGTH: 127
<212> TYPE: PRT
<213> ORGANISM: Artificial
<220> FEATURE:
<223> OTHER INFORMATION: IL-21 variant

<400> SEQUENCE: 8

Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
            50                  55                  60

Arg Ile Ile Asn Val Ser Leu Lys Arg Leu Asp Arg Asn Leu Trp Gly
 65                  70                  75                  80

Leu Ala Gly Leu Asn Ser Cys Pro Ser Cys Asp Ser Tyr Glu Lys Lys
                85                  90                  95

Pro Pro Lys Glu Phe Leu Glu Arg Phe Lys Ser Leu Leu Gln Lys Met
            100                 105                 110

Ile His Gln His Leu Ser Ser Arg Thr His Gly Ser Glu Asp Ser
            115                 120                 125

<210> SEQ ID NO 9
<211> LENGTH: 127
<212> TYPE: PRT
<213> ORGANISM: Artificial
<220> FEATURE:
<223> OTHER INFORMATION: IL-21 variant

<400> SEQUENCE: 9

Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
            50                  55                  60

Arg Ile Ile Asn Val Ser Leu Lys Arg Leu Asp Arg Asn Leu Trp Gly
 65                  70                  75                  80

Leu Ala Gly Leu Asn Ser Cys Pro Ser Cys Asp Ser Tyr Glu Lys Lys
                85                  90                  95
```

-continued

```
Pro Pro Lys Glu Phe Leu Glu Arg Phe Lys Ser Leu Leu Gln Lys Met
            100                 105                 110
Ile His Gln His Leu Ser Ser Arg Thr His Gly Ser Glu Asp Ser
            115                 120                 125
```

<210> SEQ ID NO 10
<211> LENGTH: 126
<212> TYPE: PRT
<213> ORGANISM: Artificial
<220> FEATURE:
<223> OTHER INFORMATION: IL-21 variant

<400> SEQUENCE: 10

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Asn Leu Trp Gly
65                  70                  75                  80

Leu Ala Gly Leu Asn Ser Cys Pro Val Asp Ser Tyr Glu Lys Lys Pro
                85                  90                  95

Pro Lys Glu Phe Leu Glu Arg Phe Lys Ser Leu Leu Gln Lys Met Ile
            100                 105                 110

His Gln His Leu Ser Ser Arg Thr His Gly Ser Glu Asp Ser
        115                 120                 125
```

<210> SEQ ID NO 11
<211> LENGTH: 134
<212> TYPE: PRT
<213> ORGANISM: Artificial
<220> FEATURE:
<223> OTHER INFORMATION: IL-21 variant

<400> SEQUENCE: 11

```
Met Gln Gly Gln Asp Arg His Met Ile Arg Met Arg Gln Leu Ile Asp
1               5                   10                  15

Ile Val Asp Gln Leu Lys Asn Tyr Val Asn Asp Leu Val Pro Glu Phe
            20                  25                  30

Leu Pro Ala Pro Glu Asp Val Glu Thr Asn Cys Glu Trp Ser Ala Phe
        35                  40                  45

Ser Cys Phe Gln Lys Ala Gln Leu Lys Ser Ala Asn Thr Gly Asn Asn
    50                  55                  60

Glu Arg Ile Ile Asn Val Ser Ile Lys Lys Leu Lys Arg Lys Pro Pro
65                  70                  75                  80

Ser Thr Asn Ala Gly Arg Arg Gln Lys His Arg Leu Thr Cys Pro Ser
                85                  90                  95

Cys Asp Ser Tyr Glu Lys Lys Pro Pro Lys Glu Phe Leu Glu Arg Phe
            100                 105                 110

Lys Ser Leu Leu Gln Lys Met Ile His Gln His Leu Ser Ser Arg Thr
        115                 120                 125

His Gly Ser Glu Asp Ser
        130
```